(12) United States Patent
Wagner (10) Patent No.: US 10,188,680 B2
(45) Date of Patent: *Jan. 29, 2019

(54) TUMOR LYSATE LOADED PARTICLES (71) Applicant: Orbis Health Solutions LLC, Greenville, SC (US)

(72) Inventor: Thomas E. Wagner, Greenville, SC (US)

(73) Assignee: Orbis Health Solutions LLC, Greenville, SC (US)

(*) Notice: Subject to any disclaimer, the term of this patent is extended or adjusted under 35 U.S.C. 154(b) by 0 days.

This patent is subject to a terminal disclaimer.

(21) Appl. No.: 15/656,067

(22) Filed: Jul. 21, 2017

(65) Prior Publication Data

US 2017/0319620 A1    Nov. 9, 2017

Related U.S. Application Data

(63) Continuation of application No. 14/019,025, filed on Sep. 5, 2013, now Pat. No. 9,744,193.

(60) Provisional application No. 61/697,498, filed on Sep. 6, 2012.

(51) Int. Cl.
| | | |
|---|---|---|
| A61K 35/15 | (2015.01) | |
| A61K 39/00 | (2006.01) | |
| A61K 45/06 | (2006.01) | |
| A61K 47/00 | (2006.01) | |
| C12N 5/0784 | (2010.01) | |

(52) U.S. Cl.
CPC .......... *A61K 35/15* (2013.01); *A61K 39/0011* (2013.01); *C12N 5/0639* (2013.01); *A61K 2039/5154* (2013.01); *A61K 2039/572* (2013.01)

(58) Field of Classification Search
None
See application file for complete search history.

(56) References Cited

U.S. PATENT DOCUMENTS

| | | | |
|---|---|---|---|
| 4,454,110 A | 6/1984 | Caslavsky et al. | |
| 4,563,351 A | 1/1986 | Casvalsky et al. | |
| 5,032,401 A | 7/1991 | Jamas et al. | |
| 5,340,740 A | 8/1994 | Petitte et al. | |
| 5,607,677 A | 3/1997 | Jamas et al. | |
| 7,740,861 B2 | 6/2010 | Ostroff | |
| 8,926,994 B2 | 1/2015 | Serda et al. | |
| 2001/0006623 A1 | 7/2001 | Warford, III et al. | |
| 2005/0059151 A1 | 3/2005 | Bosch | |
| 2005/0158856 A1 | 7/2005 | Edelson et al. | |
| 2005/0281781 A1 | 12/2005 | Ostroff | |
| 2006/0083718 A1 | 4/2006 | Ginns et al. | |
| 2006/0104986 A1 | 5/2006 | Duke et al. | |
| 2006/0140983 A1 | 6/2006 | Palucka et al. | |
| 2008/0167268 A1 | 7/2008 | Yan | |
| 2008/0254537 A1 | 10/2008 | Boynton et al. | |
| 2009/0209624 A1 | 8/2009 | Ginns et al. | |
| 2009/0226528 A1 | 9/2009 | Czech et al. | |
| 2010/0040656 A1 | 2/2010 | Franklin et al. | |
| 2010/0111985 A1 | 5/2010 | Schwamberger et al. | |
| 2010/0136102 A1 | 6/2010 | Franklin et al. | |
| 2010/0166751 A1 | 7/2010 | Ostroff et al. | |
| 2010/0221357 A1 | 9/2010 | Ostroff | |
| 2011/0111985 A1 | 5/2011 | Lakey et al. | |
| 2012/0070376 A1 | 3/2012 | Ostroff et al. | |
| 2013/0052220 A1 | 2/2013 | Duke et al. | |
| 2014/0363872 A1 | 12/2014 | Jaroch et al. | |

FOREIGN PATENT DOCUMENTS

| | | | |
|---|---|---|---|
| JP | 408143447 A | 6/1996 | |
| WO | WO 99/30629 A1 | 6/1999 | |
| WO | WO 02/39951 A2 | 5/2002 | |
| WO | WO 2004/021994 A2 | 3/2004 | |
| WO | WO 2007/092792 A2 | 8/2007 | |
| WO | WO2009102465 * | 8/2009 | ............ A61K 48/00 |
| WO | WO 2011/053331 A1 | 5/2011 | |
| WO | WO 2011/131472 A1 | 10/2011 | |
| WO | WO 2012/082450 A2 | 6/2012 | |
| WO | WO 2014/040089 A1 | 3/2014 | |
| WO | WO 2015/030613 A1 | 3/2015 | |

OTHER PUBLICATIONS

U.S. Appl. No. 14/019,007, filed Sep. 5, 2013, Wagner.
U.S. Appl. No. 14/103,116, filed Dec. 11, 2013, Wagner.
U.S. Appl. No. 14/019,025, filed Sep. 5, 2013, Thomas E. Wagner.
U.S. Appl. No. 15/252,999, filed Aug. 31, 2016, Wagner.
U.S. Appl. No. 15/123,479, filed Sep. 2, 2016, Wagner.
Cole et al., "Novel Strategies to Enhance Vaccine Immunity against Coccidioidomycosis," PLOS Pathogens, Dec. 2013, 9(12):e1003768, 1-4.
Colino et al., "Dendritic Cells Pulsed with Intact *Streptococcus pneumonia* Elicit both Protein- and Polysaccharide-specific Immunoglobulin Isotype Responses In Vivo through Distinct Mechanisms," J. Exp. Med., Jan. 7, 2002, 195(1):1-13.
Day et al., Eds., "Cryopreservation and Freeze-Drying Protocols," Methods in Molecular Biology, Second Ed., 2007, p. 10, Table 4.
De Nobel et al., "Increased Cell Wall Porosity in *Saccharomyces cerevisiae* after Treatment with Dithiothreitol or EDTA," Journal of General Microbiology, 1989, 135:2077-2084.
Figueiredo et al., "Yeast cell wall particles: a promising lass of nature-inspired microcarriers for multimodal imaging," Chem. Commun., 2011, 47:10635-10637.
Foged et al., "Particle size and surface charge affect particle uptake by human dendritic cells in an in vitro model," International Journal of Pharmaceutics, 2005, 298:315-322.
Jain et al., "Targeted drug delivery to macrophages," Expert Opinion on Drug Delivery, 2013, 10(3):353-367.
PubChem, 2015, Compound Summary for CID 6517 "Tetraethyl orthosilicate," 49 pages.
Soto et al., "Glucan Particles for Macrophage Targeted Delivery of Nanoparticles," Journal of Drug Delivery, vol. 2012 (2011), Article ID 143524, 13 pages.

(Continued)

*Primary Examiner* — Karen A. Canella
(74) *Attorney, Agent, or Firm* — Foley & Lardner LLP (57) ABSTRACT

Dendritic cells containing tumor lysate loaded particles are prepared. The dendritic cells present tumor antigens to elicit the Major Histocompatibility Complex class I pathway and can be used as a vaccine to treat cancer, including ocular melanoma.

14 Claims, 7 Drawing Sheets

(56) References Cited

OTHER PUBLICATIONS

Strome et al., "Strategies for Antigen Loading of Dendritic Cells to Enhance the Antitumor Immune Response," Cancer Research, Mar. 15, 2002, 62:1884-1889.
Xia et al., "Porous Silicon Microparticle Potentiates Anti-Tumor Immunity by Enhancing Cross-Presentation and Inducing Type I Interferon Response," Cell Reports, 2015, 11:957-966.
Huang et al., "Robust Stimulation of Humoral and Cellular Immune Responses following Vaccination with Antigen-Loaded β-Glucan Particles," MBio, Jul./Aug. 2010, 1(3):e00164-10, 1-7.
Kotera et al., "Comparative Analysis of Necrotic and Apoptotic Tumor Cells As a Source of Antigen(s) in Dendritic Cell-based Immunization," Cancer Research, Nov. 15, 2001, 61:8105-8109.
Sauter et al., "Consequences of Cell Death: Exposure to Necrotic Tumor Cells, but Not Primary Tissue Cells or Apoptotic Cells, Induces the Maturation of Immunostimulatory Dendritic Cells," J. Exp. Med., Feb. 7, 2000, 191(3):423-433.
Soto et al., "Characterization of Multilayered Nanoparticles Encapsulated in Yeast Cell Wall Particles for DNA Delivery," Bioconjugate Chem., 2008, 19:840-848.
Goforth et al., "Immune stimulatory antigen loaded particles combined with depletion of regulatory T-cells induce potent tumor specific immunity in a mouse model of melanoma," Cancer Immunol. Immunother., 2009, 58:517-530.
U.S. Appl. No. 15/751,640. filed Aug. 10, 2016, Wagner.
Huang et al., "Characterization and Optimization of the Glucan Particle-Based Vaccine Platform," Clinical and Vaccine Immunology, Oct. 2013, 20(10):1585-1591.

\* cited by examiner

TUMOR LYSATE LOADED PARTICLES

CROSS-REFERENCE TO RELATED APPLICATIONS

This application is a Continuation of U.S. application Ser. No. 14/019,025, filed Sep. 5, 2013, which claims priority from U.S. provisional application No. 61/697,498, filed Sep. 6, 2012.

BACKGROUND OF THE INVENTION

A tumor cell exists in part because it has selected for one or more mutations that allows it to partially or completely escape immune surveillance in vivo.

In an attempt to elicit an immune response to a tumor cell, previous researchers have used dendritic cells, which are professional antigen-presenting cells, to present tumor antigens to the immune system. For example, dendritic cells pulsed with peptide or tumor lysate have been used to vaccinate melanoma patients.

However, simply presenting tumor antigens to the immune system in the foregoing manner has not been effective because such antigens were merely endocytosed by the dendritic cells and generally presented through the Major Histocompatibility Complex (MHC) class II, which elicits only helper T cells and does not provide a robust immune response.

In contrast, presenting tumor antigens via the MHC class I pathway contributes to a more robust anti-tumor immunity by activating CD8+ T cells. Previous researchers have attempted to present tumor antigens through the MHC class I pathway by using gene transfer methods. However, these methods have disadvantages, including (1) a limited ability to identify all of the important tumor-specific antigens, (2) a limited ability to map the genes of specific tumor antigens, (3) only one or a small number of known tumor antigen genes can be introduced into a dendritic cell and (4) the methods are time-consuming and cumbersome.

SUMMARY OF THE INVENTION

Some embodiments relate to an isolated dendritic cell comprising a phagocytosed component consisting essentially of (i) a particle and (ii) a tumor lysate loaded within the particle. In specific embodiments, the tumor lysate is present in an amount from about 200 µg to about 500 µg. In specific embodiments, the tumor lysate is present in an amount of about 200 µg.

In some embodiments, the tumor lysate is a lysate selected from a cancer selected from the group consisting of breast cancer, small cell lung cancer, non-small cell lung cancer, glioma, medulloblastoma, neuroblastoma, Wilms tumors, rhabdomyosarcoma, osteosarcoma, liver cancer, pancreatic cancer, melanoma, prostate cancer and ocular melanoma.

In some embodiments, the particle is a yeast cell wall particle. In some embodiments, the dendritic cell is an immature cell that has been isolated for no more than 8 days.

Another embodiment relates to a vaccine comprising the foregoing isolated dendritic cell.

Some embodiments relate to a method for producing an isolated dendritic cell containing a tumor lysate loaded particle comprising: (i) loading the tumor lysate into the particle to produce the tumor lysate loaded particle; (ii) freeze-drying the tumor lysate loaded particle; and (iii) incubating the tumor lysate loaded particle with a dendritic cell, wherein the incubating causes the dendritic cell to phagocytose the tumor lysate loaded particle.

In specific embodiments, the foregoing method further comprises (a) resuspending the tumor lysate loaded particle in solution and (b) freeze-drying the resuspended solution before step (iii). In specific embodiments, the tumor lysate is produced by freezing and thawing the tumor. In specific embodiments, the foregoing method further comprises repeating the freezing and thawing steps. In specific embodiments, the foregoing method further comprises cryopreserving the tumor lysate at −150° C.

In specific embodiments, step (iii) comprises: (a) adding tumor lysate into a yeast cell wall particle, (b) incubating the yeast cell wall particle, (c) freeze-drying the yeast cell wall particle and (d) washing the yeast cell wall, wherein steps (b)-(c) are repeated at least once with a step of adding water into the yeast cell particle before step (b) is repeated.

In specific embodiments, step (iii) comprises: (a) contacting the tumor lysate loaded particle and the dendritic cell at a ratio of about 100:1, (b) incubating the tumor lysate loaded particle with the dendritic cell for 1 to 2 hours and (c) collecting the dendritic cell and washing the cell.

In a preferred embodiment, a small amount of one or more immune response enhancing adjuvants is added to the tumor lysis buffer prior to incubating with a dendritic cell. The addition of one or more adjuvants increases the effects of the tumor lysate on the dendritic cell while dramatically decreasing any systemic effects from such adjuvants. Commonly used adjuvants include but are not limited to proteins, peptides, nucleic acids and carbohydrates.

Exemplary adjuvants include but are not limited to monophosphoryl lipid A, GpC olognonucleotides (such as GpC DNA), Poly I:C, Poly ICLC, potent MEW II epitope peptides, beta glucan, and dendritic cell stimulating cytokines such as IL-12. Suitable adjuvants are those molecules known to interact with receptors on dendritic cells in order to activate dendritic cells and further stimulate a more robust generation of T cells, such as CD4+ and CD8+ T cells.

In one embodiment, the amount of one or more immune response enhancing adjuvants is at least about 5 µg, at least about 10 µg, at least about 15 µg, at least about 20 µg, at least about 25 µg, at least about 30 µg, at least about 35 µg, at least about 40 µg, at least about 45 µg, at least about 50 µg, at least about 60 µg, at least about 70 µg, at least about 80 µg, at least about 80 µg, at least about 90 µg, or at least about 100 µg. In one embodiment, the amount of adjuvant represents between 1-10% of the total lysate amount. The amount of adjuvant is sufficient to stimulate receptors, such as the toll-like receptor, on the dendritic cell.

Some embodiments relate to a method for treating cancer, comprising administering a vaccine comprising the foregoing isolated dendritic cell. In specific embodiments, the cancer is selected from the group consisting of breast cancer, small cell lung cancer, non-small cell lung cancer, glioma, medulloblastoma, neuroblastoma, Wilms tumors, rhabdomyosarcoma, osteosarcoma, liver cancer, pancreatic cancer, melanoma, prostate cancer and ocular melanoma.

DETAILED DESCRIPTION OF THE PREFERRED EMBODIMENTS

Reference is made herein to various methodologies known to those of ordinary skill in the art. Publications and other materials setting forth such known methodologies to which reference is made are incorporated herein by reference in their entirety as though set forth in full.

As used herein, the singular forms "a," "an," and "the" designate both the singular and the plural, unless expressly stated to designate the singular only. Likewise, singular forms of terms designate both the singular and plural, unless expressly stated to designate the singular only. For example, "vaccine" means "vaccine" or "vaccines."

The term "about" in connection with numerical values and ranges means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used.

As used herein "subject" or "patient" denotes any animal in need of treatment with a vaccine. For example, a subject may be suffering from or at risk of developing a condition that can be treated or prevented with a vaccine. As used herein "subject" or "patient" includes humans.

As used herein, the phrases "therapeutically effective amount" and "therapeutic level" mean that vaccine dosage or plasma concentration in a subject, respectively, that provides the specific response for which the vaccine is administered in a subject in need of such treatment. For convenience only, exemplary dosages, vaccine delivery amounts, therapeutically effective amounts and therapeutic levels are provided below with reference to adult human subject. Those skilled in the art can adjust such amounts in accordance with standard practices as needed to treat a specific subject and/or condition/disease.

Tumor Lysate

As described herein, "tumor lysate" refers to a tumor that has been lysed. Tumor lysis can occur under a number of conditions, including repeated freezing and thawing of the tumor, physical breakage of the tumor by homogenizing, contact with a hyper- or hypo-tonic solution and contact with one or more non-ionic detergents. The tumor lysate is not cross-linked during the lysing process. In another embodiment, the tumor lysate is produced by mincing, grinding or mashing the tumor, or otherwise pulverizing the tumor using any known technique in the art. In another embodiment, the tumor lysate is produced by mincing, grinding, mashing or pulverizing the tumor in the presence of phosphate buffer solution (PBS), such as 1×PBS.

In specific embodiments, the tumor lysate is produced from a solid tumor weighing a minimum of 200 to 500 µg.

In another embodiment, the tumor lysate is produced by mincing, grinding, mashing or pulverizing the tumor followed by repeated freezing and thawing. In specific embodiments, the minced tumor is frozen and thawed multiple times. In specific embodiments, the minced tumor is frozen and thawed at least 1, 2, 3 or 4 times. In some embodiments, the freezing is performed in liquid nitrogen, and can be performed for 20 minutes. In specific embodiments, the thawing is performed at room temperature. In another embodiment, the tumor lysate is stored at a temperature of about −135° C. or below after the freezing and thawing process. In specific embodiments, the tumor lysate is store at a temperature of −150° C. or below after the freezing and thawing process.

The tumor lysate can be prepared from any solid tumor including, but not limited to carcinomas, and sarcomas. In some embodiments, the solid tumors are from tumors relating to breast cancer, small cell lung cancer, non-small cell lung cancer, glioma, medulloblastoma, neuroblastoma, Wilms tumors, rhabdomyosarcoma, osteosarcoma, liver cancer, pancreatic cancer, melanoma, prostate cancer and ocular melanoma.

A number of immune response enhancing agents can be added to the tumor lysis buffer as adjuvants to boost immune response such that when the tumor lysate is incubated with a dendritic cell, the adjuvants exhibit an increased effect on the dendritic cell while dramatically decreasing any systemic effects from such adjuvants.

It is within the purview of one of ordinary skill in the art to select one or more suitable adjuvants for this invention. For instance, monophosphoryl lipid A, GpC oligonucleotides, Poly I:C, Poly ICLC, potent MHC II epitope peptides, and dendritic cell stimulating cytokines such as IL-12, IL-2, and GM-CSF are good adjuvant candidates of this invention.

Particle

As described herein, "particle" refers to any hollow and porous structure that can contain tumor lysate therein and also allow the lysate to exit the structure. In some embodiments, the size of the particle is about 0.5 to about 5 µm, which approximates the size of bacterium to allow the particle to be ingested by monocytes, such as dendritic cells. In specific embodiments, the size of the particle is about 0.5 to about 1 µm. In specific embodiments, the size of the particle is about 0.5 to about 2.5 µm. In some embodiments, the particle can be any particle with a glycan network, so long as the particle is about 0.5 to about 5 µm in size.

In some embodiments, the particle is a bead vector. The bead vector is not limited by shape or material, but can be any shape, size or material that allows the bead vector to be phagocytosed by monocytes, including dendritic cells.

In another embodiment, the particle is a yeast cell wall particle ("YCWP"). The YCWP is prepared from yeast cell wall such that the particle is porous and can contain lysate therein. In one embodiment, the YCWP is prepared from *Saccharomyces cerevisiae*. In another embodiment, the YCWP is a zymosan particle. In another embodiment, the YCWP approximates the size of microbial structures that cells of the mononuclear phagocyte system and other phagocytic cells typically ingests. In specific embodiments, the YCWP is about 1-5 µm.

In one embodiment, the YCWP is prepared by (a) suspending yeast to produce a suspension, (b) incubating the suspension, (c) centrifuging the suspension and removing the supernatant and (d) recovering the resulting YCWP. In another embodiment, steps (a)-(d) are repeated at least 1, 2, 3 or 4 times.

In another embodiment, the YCWP is prepared by (a) suspending yeast in a solution to produce a first suspension, (b) incubating the first suspension, (c) centrifuging the first suspension and removing the supernatant, (d) suspending the resulting pellet to produce a second suspension, (e) incubating the second suspension, (f) centrifuging the second suspension and removing the supernatant and (g) washing the resulting pellet to recover the YCWP. In another embodiment, the YCWP is sterilized.

In specific embodiments, the yeast is suspended in NaOH, including 1M NaOH. In specific embodiments, the first suspension is incubated at about 80° C. for about 1 hour or for 1 hour. In specific embodiments, the centrifuging is performed at about 2000 times gravity for about 10 minutes, or at 2000 times gravity for 10 minutes. In specific embodiments, the pellet is suspended in water, including water at about pH 4.5 or at pH 4.5. In specific embodiments, the second suspension is incubated at about 55° C. for about 1 hour or at 55° C. for 1 hour. In specific embodiments, the pellet is washed in water at least 1, 2, 3 or 4 times. In specific embodiments, the pellet is washed once.

In another embodiment, the YCWP is sterilized using isopropanol and/or acetone following washing of the pellet. In specific embodiments, other known alcohols are appropriate. In specific embodiments, the YCWP is allowed to fully dry after sterilization. In another embodiment, the YCWP is resuspended after being allowed to dry. In specific embodiments, the YCWP is resuspended in PBS, such as 1×PBS. In another embodiment, the YCWP is allowed to dry and then frozen before the tumor lysate is loaded into the YCWP, in order to place it in storage before use. In specific embodiments, the YCWP is freeze dried and store at about 4° C. or lower. In specific embodiments, the YCWP is freeze dried and store at 4° C.

Tumor Lysate Loaded Particle

The particle is loaded with tumor lysate. In one embodiment, the tumor lysate is loaded into the particle by incubating the lysate and a suspension of particles together and allowing the lysate to penetrate into the hollow insides of the particles.

In another embodiment, after the particle is loaded with tumor lysate, the combination is freeze-dried to create an anhydrous tumor lysate within the particle. By freeze-drying the particle loaded with tumor lysate, the lysate is trapped within the particle and ready to be phagocytosed by a monocyte, such as a dendritic cell. In specific embodiments, the freeze-drying is the only mechanism used to trap the lysate within the particle. In specific embodiments, the entrapment is not caused by a separate component blocking the lysate from exiting the particle, for example, by physical entrapment, hydrophobic binding, any other binding. In specific embodiments, the entrapment is not caused by crosslinking or otherwise attaching the lysate to the particle outside of any attachment that may occur upon freeze-drying.

In another embodiment, the particle is resuspended in solution after the freeze-drying. In specific embodiments, the solution is water. In specific embodiments, the particle is resuspended to allow additional tumor lysate to penetrate the particle and then the combination is freeze-dried again. In other embodiments, the combination is subjected to multiple freeze-drying and resuspensions. In other embodiments, the tumor lysate loaded particle is sterilized in ethanol after the freeze-drying and before use.

In specific embodiments, the tumor lysate is loaded into the particle by (a) incubating the lysate and a suspension of the particles, allowing the lysate to penetrate into the hollow insides of the particles and freeze-drying the suspension of particles loaded with lysate and (b) optionally resuspending the particles, incubating the resuspended particles and freeze drying the resuspended particles and any tumor lysate not already in the particle.

In specific embodiments using YCWPs, the number of YCWPs is about $1\times10^9$ and the volume of tumor lysate is about 50 μL (generated from about 200 μg of tumor tissue). In specific embodiments, the number of YCWPs is $1\times10^9$ and the volume of tumor lysate is 50 μL (from about 200 μg of tumor tissue). In specific embodiments, the incubation in step (a) is for about 2 hours at about 4° C. In specific embodiments, the incubation in step (a) is for 2 hours at 4° C. In some embodiments, the foregoing suspension is freeze dried in step (b) over a period of about 2 hours or over a period of 2 hours. In some embodiments, the YCWPs in step (c) are resuspended in water, including about 50 μL of water or 50 μL of water. In some embodiments, the resuspended YCWPs are incubated in step (d) for about 2 hours at about 4° C. or for 2 hours at 4° C.

Dendritic Cell

As described herein, "dendritic cell" refers to a cell generated from a peripheral blood mononuclear cell ("PBMC"). In one embodiment, a dendritic cell is prepared by (a) collecting blood, (b) diluting the blood, (c) performing a density gradient separation of PBMCs, (d) lysing red blood cells and washing the PBMCs, (e) incubating the PBMCs, (f) removing nonadherent cells and (g) culturing adherent cells in media.

In some embodiments, the dendritic cell is an immature dendritic cell that has been cultured for no more than 5 days. In other embodiments, the dendritic cell has been cultured for 6-8 days.

In specific embodiments, the blood is heparinized. In specific embodiments, the density gradient separation at step (c) comprises placing the blood in a Lymphocyte Separation Medium and then centrifuging the blood. In specific embodiments, the centrifuging is performed at about 1000 times gravity for about 20 minutes or at 1000 times gravity for 20 minutes. In specific embodiments, a second centrifuging is performed before step (d) and is performed at about 500 g for about 5 minutes or is performed at 500 g for 5 minutes. In specific embodiments, a third centrifuging is performed before step (d) and is performed at about 500 g for about 10 minutes or is performed at 500 g for 10 minutes. In specific embodiments, the lysing is performed using an ACK lysing solution, followed by incubation, preferably at room temperature for about 5 minutes, and followed by a subsequent centrifugation. In specific embodiments, the PBMCs are washed in RPMI-1640 medium. In specific embodiments, the PBMCs are incubated at step (e) in flasks at about 37° C. for about 1-2 hours or at 37° C. for 1-2 hours. In specific embodiments, serum-free DC media is added to the flask.

In some embodiments, one or more cytokines is present in the culture media, including, but not limited to, granulocyte macrophage colony stimulating factor (800 units/ml) and IL-4 (500 units/ml).

Tumor Lysate Loaded Particles Phagocytosed in Dendritic Cells

The tumor lysate loaded particle is phagocytosed within a monocyte, preferably a dendrite cell. In one embodiment, the tumor lysate loaded particle is incubated with a dendritic cell such that the cell phagocytoses the tumor lysate loaded particle.

In specific embodiments, the particle is incubated with the dendritic cell at a ratio of about 100:1 or at a ratio of 100:1. The incubation can be performed for in about 1 hour, 1 hour or preferably less than 1 hour.

In specific embodiments, the incubated dendritic cell containing the tumor lysate particle is collected and washed, for example, at least 1, 2, 3 or 4 times. In other embodiments, the dendritic cells are incubated after washing and resuspended in freezing medium. In specific embodiments, the resuspension produces a concentration of about $10\times10^6$ cells per ml or $10\times10^6$ cells per ml. In specific embodiments, the resuspension is frozen for storage before use.

Vaccine

In one embodiment, the dendritic cell containing a tumor lysate loaded particle is used as a vaccine to prevent and/or treat a disease, including cancer. The disease to be treated is not particularly limiting, but depends on the particular tumor lysate loaded into the particle. For example, a vaccine using tumor lysate from a breast cancer tumor is used to treat breast cancer. In another embodiment, a patient's own tumor cells are used to create the vaccine. For example, the vaccine can be produced using tumor lysate from a tumor associated with breast cancer and then administered to the breast cancer patient from which the tumor was extracted. In another embodiment, about 200 μL of a $10\times10^6$ concentration of dendritic cells containing tumor lysate loaded particles forms one dose of the vaccine.

In another embodiment, the dose is administered by diluting the 200 μL aliquot to a final volume of 1 ml before administering the dose to a patient. In specific embodiments, the aliquot is diluted with sterile saline containing 5% human serum albumin. In specific embodiments, the 200 μL aliquot will need to be thawed before dilution. In such a scenario, the length of time between thawing and administration of the dose to a patient will be no longer than 2 hours. In some embodiments, the diluted aliquot is administered in a 3 cc syringe. In some embodiments, a syringe needle no smaller than 23 gauge is used.

In another embodiment, a patient is administered at least 1, 2, 3 or 4 doses. In specific embodiments, a patient is re-vaccinated once every 4 weeks. In specific embodiments, about 1-2 million dendritic cells containing tumor lysate loaded particles will be administered at each vaccination. In another embodiment, the dendritic cells containing tumor lysate loaded particles are administered to a patient by injection. In specific embodiments, the tumor lysate loaded particles are injected in a patient at or near (1) a tumor or (2) a lymph node.

In some embodiments, the vaccine is not administered with any other immunosuppressive treatment, such as steroids or chemotherapy. The vaccine can be administered using any technique, including intravenous injection and inhalation.

The vaccine can also contain biological adjuvants, including but not limited to nucleic acids such as GpC oligonucleotides, proteins or peptide epitopes such as the tetanus toxoid MHC class II-binding p30 peptide.

Example 1: Preparing Dendritic Cells

Dendritic cells were generated from a patient's PBMCs. PBMCs were collected from the patient by a blood draw of 200 ml following standard operating procedures. The blood was then transferred to 250 ml centrifuge tubes and diluted 1:1 with 1×PBS. Then, 35 ml of the diluted blood was layered over 15 ml of room temperature Lymphocyte Separation Medium (LSM; Mediatech) in 50 ml tubes and centrifuged at 1000 g for 20 minutes at room temperature. The PBMC layers were removed by pipetting from the LSM gradients and placed into clean 50 ml centrifuge tubes. Four volumes of 1×PBS were added and the tubes were inverted to mix the contents. The PBMCs were then centrifuged at 500 g at room temperature for 5 minutes. Ten ml of 1×PBS were added into each tube and the cells were resuspended and pooled into 1 tube. The PBMCs were again centrifuged at 500 g at room temperature for 10 minutes, resuspended in 20 to 40 ml of ACK lysing solution (Cambrex) and incubated at room temperature for 5 minutes. The cells were then centrifuged again at 1500 rpm for 5 minutes. The PBMCs were resuspended in 30 ml RPMI-1640 medium (Mediatech). The cells were then transferred into 2-4 T75 flasks. The flasks were incubated at 37° C. for 1 to 2 hours. The non-adherent cells were then removed by rinsing. Afterwards, 10 ml of 1×PBS were added into each flask, the flask swirled, and the PBS removed. Afterwards, 10 ml of complete DC media (serum-free DC Medium+800 U/ml GM-CSF+1000 U/ml IL-4) was added to each flask. The flasks were then incubated at 37° C., 5% CO2 for 2 days. On Day 3, 10 ml of complete DC medium was added into each flask. The cells were then incubated for another 2 days. On Day 6 or 7, the resulting immature DCs were ready for use.

Figure 1:
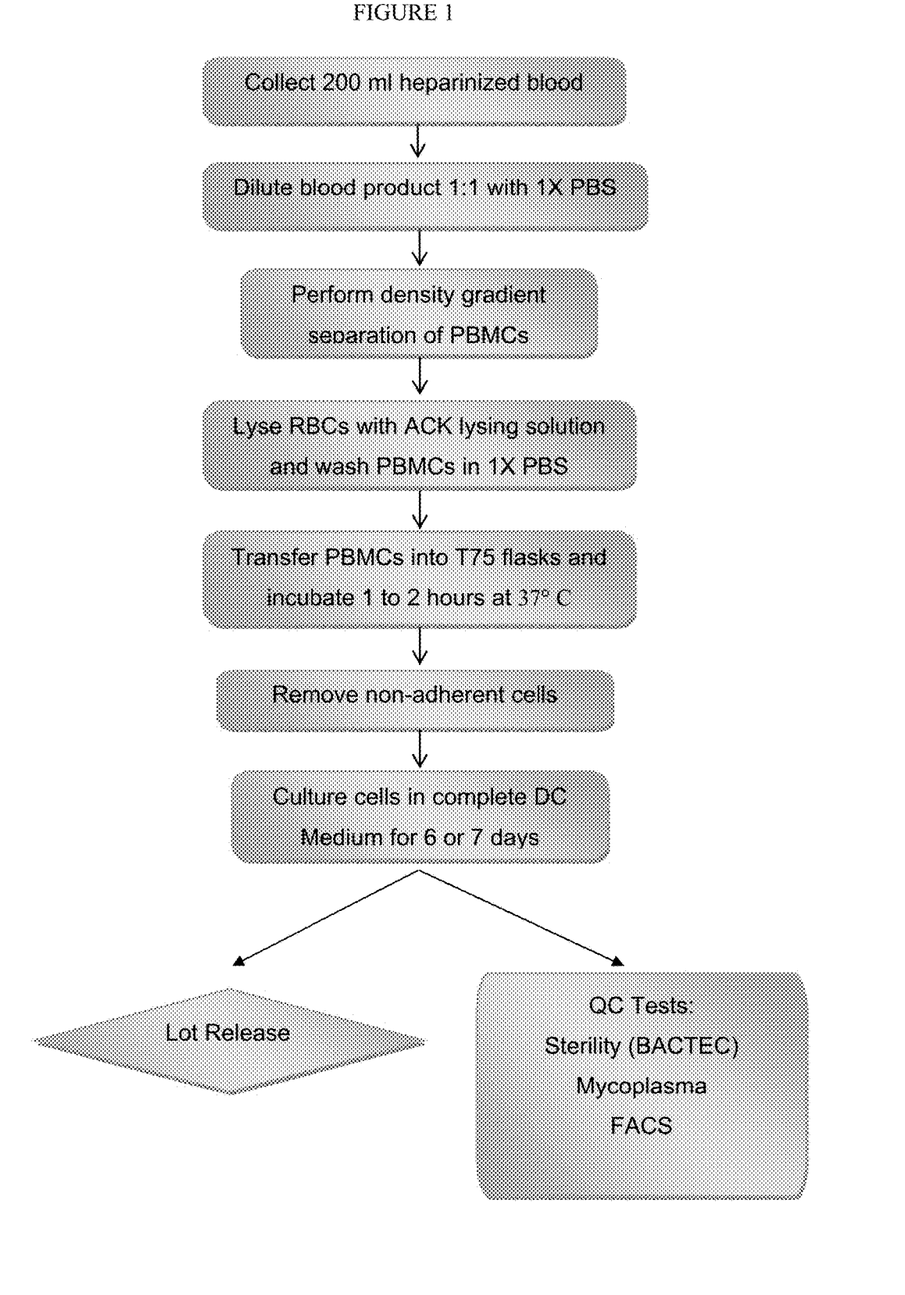
FIG. 1 depicts a process for producing dendritic cells.

FIG. 1 provides an overview of the generation of dendritic cells.

Example 2: Preparing Tumor Lysate

A tumor sample was obtained from a patient. After separating fat and necrotic tissue away from the tumor tissue, the tissue was weighed and 1×PBS added (50 μL of PBS per 200 μg of tissue) and the tumor was minced thoroughly with scalpels in 1×PBS. The tumor cells were then subjected to 4 cycles of freeze and thaw. The freezing was performed in liquid nitrogen for 20 minutes and the thawing was performed at room temperature. Prepared tumor lysate was quantified by a spectrophotometer. An aliquot was taken for quality control testing. The remainder was stored at ≤−135° C. in preparation for vaccine preparation. Small amounts of adjuvant can optionally be added after the freeze thaw cycles.

Figure 2:
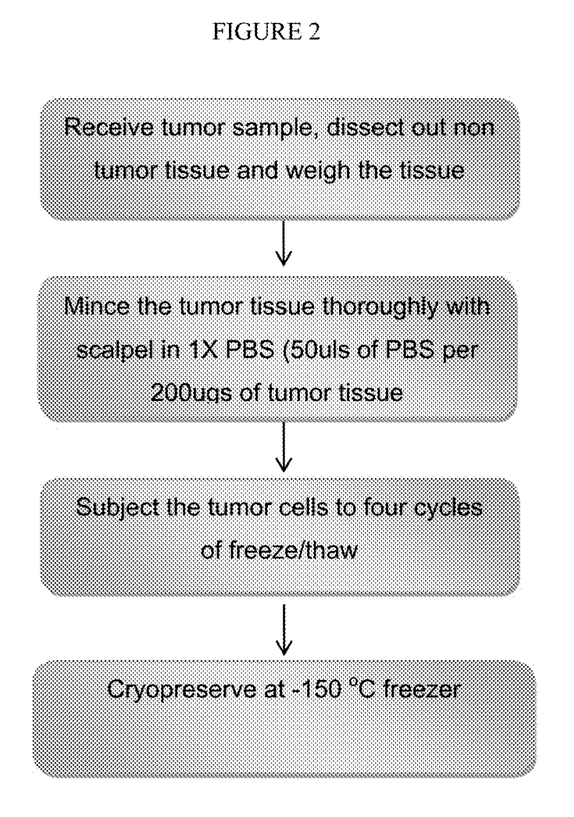
FIG. 2 depicts a process for producing tumor lysate.

FIG. 2 provides an overview of the tumor cell lysate processing.

Example 3: Preparing YCWP

YCWPs were prepared from Fleishmans Baker's Yeast or equivalent. Briefly, 10 g of Fleishmans Baker's yeast was suspended in 100 ml of 1 M NaOH and heated to 80° C. for one hour. The undissolved yeast cell walls were recovered by centrifugation at 2000×g for 10 minutes. The recovered yeast cell walls were then resuspended in 100 ml of water with the pH adjusted to 4.5 with HCl and incubated at 55° C. for an additional hour, and subsequently recovered by centrifugation. The recovered YCWPs were then washed with water once, isopropanol 4 times and finally acetone 2 times. Once the YCWPs were fully dried they were resuspended in PBS, counted, aliquoted into groups of $1\times10^9$ particles and freeze dried for use in manufacturing the vaccine.

Figure 3:
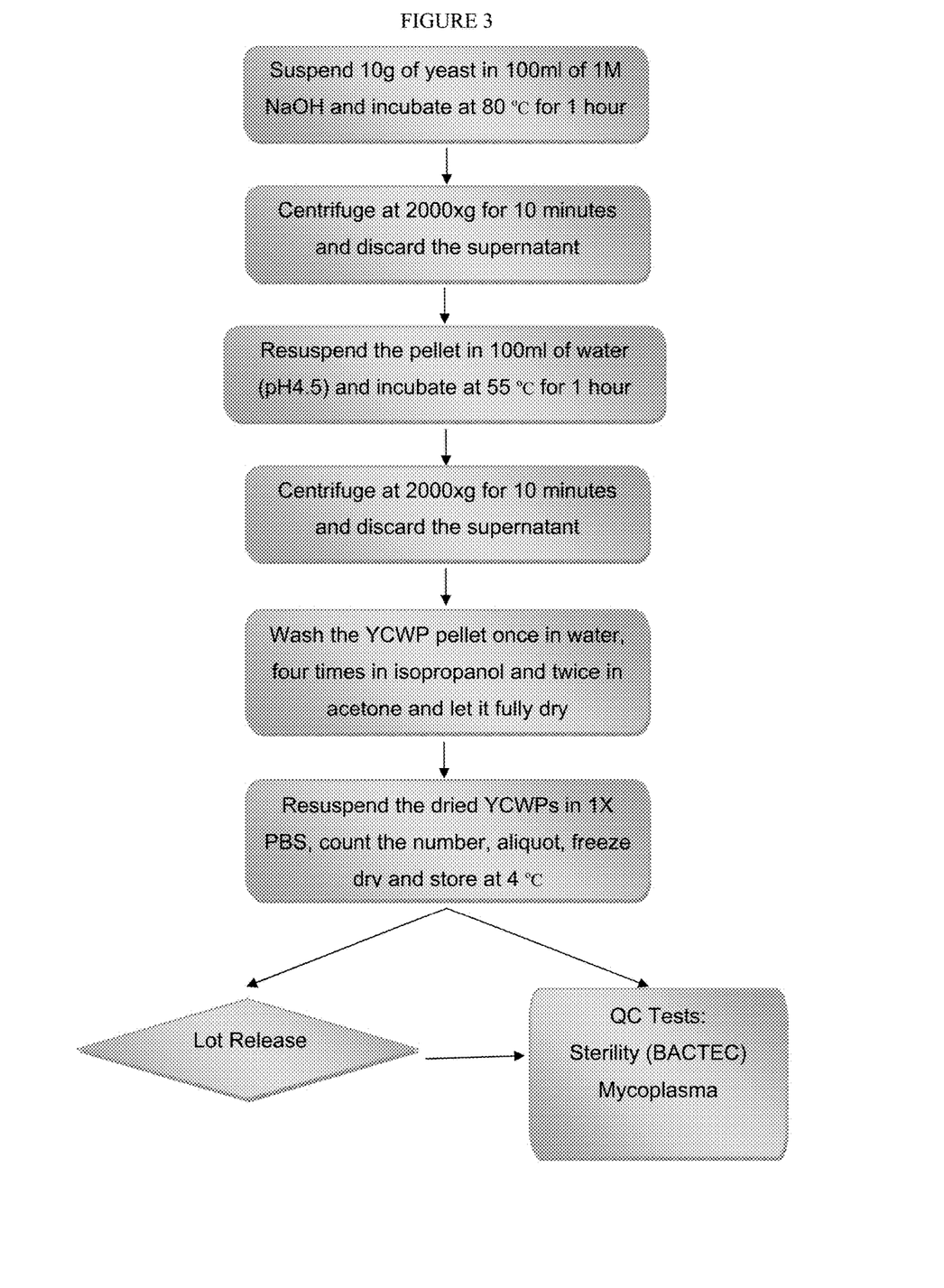
FIG. 3 depicts a process for producing yeast cell wall particles.

FIG. 3 provides an overview of the yeast cell wall particles processing.

Example 4: Preparing YCWP

Three grams of active dry yeast (Fleischmann's or equivalent) were washed three times in water by suspending the yeast in 30 mL of sterile water, vortexing, and centrifuging at 800-1000×g for 5 minutes at room temperature. After decanting the supernatant, the yeast pellet was resuspended in 50 mL of 1 M NaOH and heated in a 90° C. water bath for 1 hour.

The yeast suspension was subsequently centrifuged at 800-1000×g for 5 minutes, and the pellet was resuspended in 25-30 mL of acid water (pH adjusted to 4.5 with HCl). The acid water wash step was repeated until the pH of the suspension is <7.0. Then the pellet was resuspended in 30 mL acid water and incubated in a 75° C. water bath for 1 hour. The yeast pellet was recovered by centrifugation at 1000×g for 5 minutes, and then washed with 10 mL of sterile water 3 times, 10 mL of isopropanol 4 times and finally 10 mL of acetone 2 times. The acetone was carefully removed, and the pellet was spread evenly on the glass surface of a beaker, allowed to air dry overnight.

The dried YWCPs were collected and stored in a vacuum jar at 4° C. and then washed in 10-15 mL of filtered 70% ethanol 3 times. The YWCPs were briefly sonicated on the final wash, and the sonication was repeated if necessary to disperse clumps. Once the ethanol was removed, the YWCPs were washed in sterile water. Aliquots of 100 µl of YWCPs were dispensed into 2.0 mL rounded bottom snap top centrifuge tubes, placed in freezer for 1 hour, freeze dried, and stored in a vacuum jar at 4° C. for future use.

Example 5: Loading Tumor Lysate into YCWP

A suspension of fully anhydrous YCWPs ($1\times10^9$) was placed in contact with 50 µL of tumor lysate in PBS (from 200 µgs of tumor tissue) over a period of 2 hours at 4° C., allowing the lysate to penetrate into the hollow insides of the YCWPs to produce loaded YCWPs. The suspension was then freeze dried for 2 hours. After freeze drying, 50 µL of water was added to the loaded YCWPs, incubated for another 2 hours at 4° C. and again freeze dried to yield YCWPs with dry tumor lysate within their hollow insides. The loaded YCWPs were then sterilized by washing in ethanol and maintained in ethanol.

Figure 4:
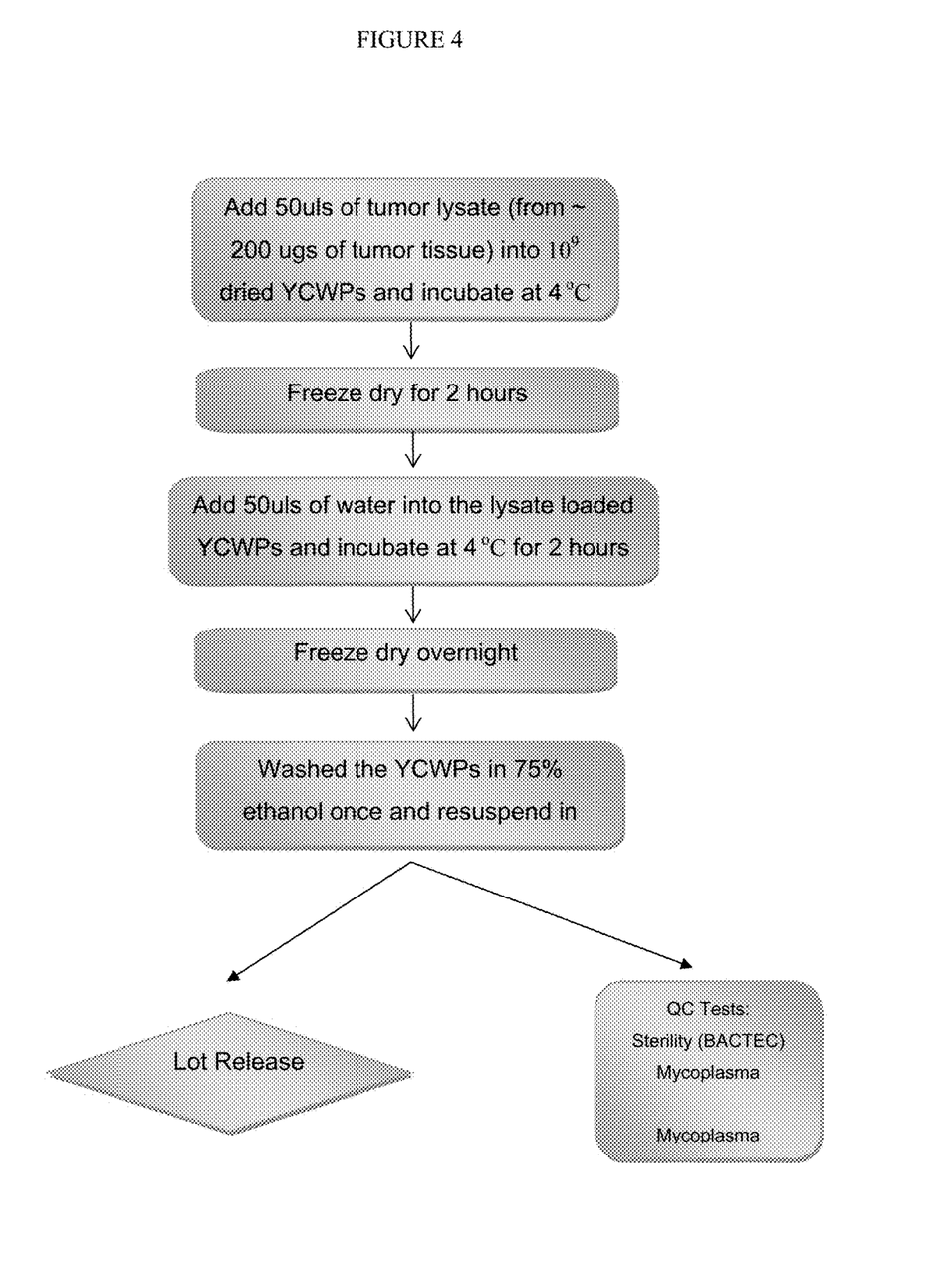
FIG. 4 depicts a process for loading tumor lysate into yeast cell wall particles.
Figure 5:
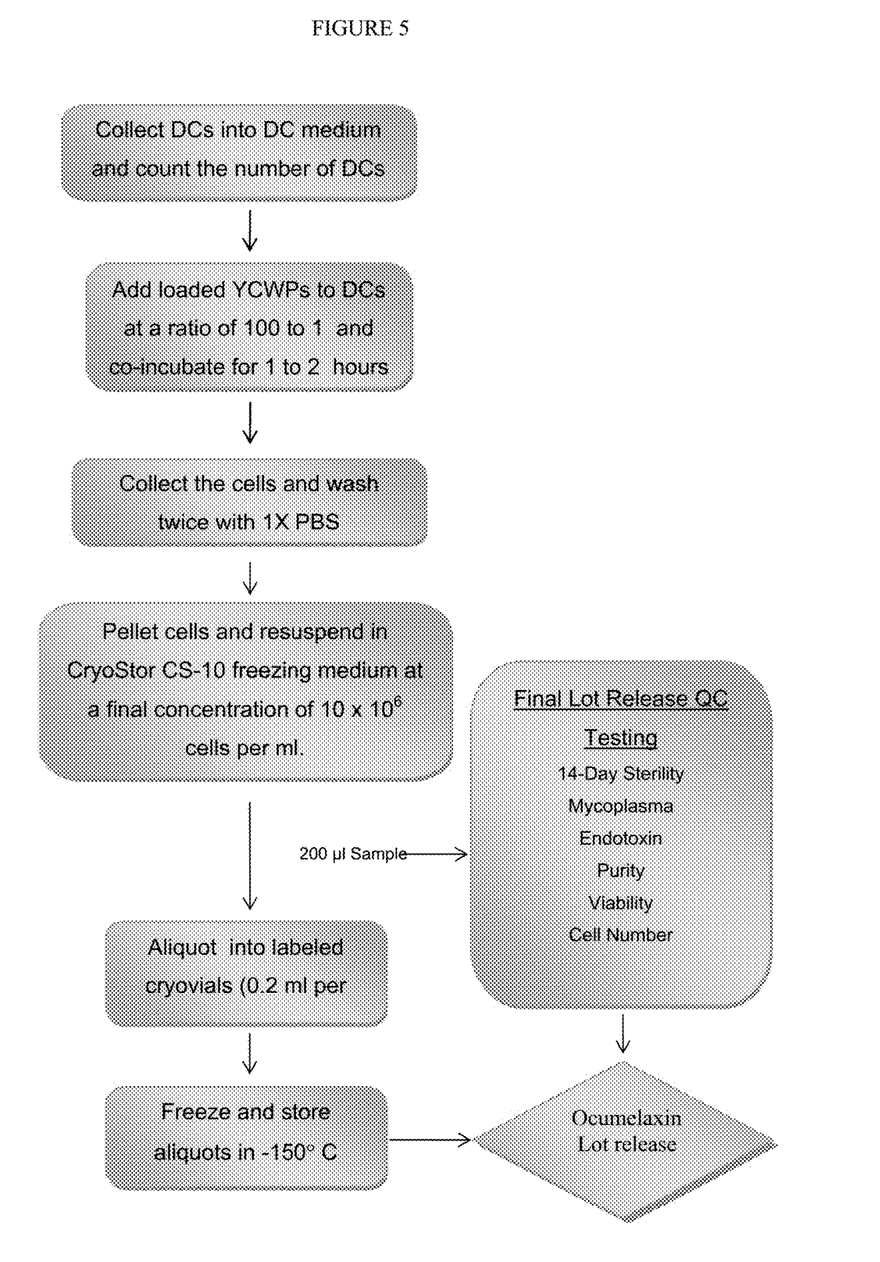
FIG. 5 depicts a process for producing tumor lysate particle loaded dendritic cells.

FIG. 4 provides an overview of the YCWPs loading procedure.

Example 6: Loading YCWPs with Tumor Lysate

A patient tumor biopsy sample was mixed carefully with 50-100 µl of lysis buffer (PBS) (depending on the amount of the tumor sample), avoiding bubbles during mixing, and was then incubated at 4° C. for 30 minutes. The mixture was subjected to freeze-thaw 3 times in acetone-dry ice bath and 37° C. water bath, and centrifuged at 4° C. for 10 minutes at maximum speed. 50 µl of the prepared tumor lysate was added in a sterile 2 mL centrifuge tube containing 10 mg of dried YCWPs such that the liquid tumor lysate covered the YCWPs. The mixture was incubated at 4° C. for 2 hours until the liquid tumor lysate soaked into the YCWPs.

The tube was then placed into a −85° C. freezer for 30 minutes for a quick freeze of the pellet. The tube was placed on freeze drier overnight. 50 µl of sterile water was added onto the dried yeast pellet and incubated at 4° C. for 2 hours to allow the liquid to soak into the pellets.

The tube was placed into a −85° C. freezer for 30 minutes for a quick freeze of the pellet. The tube was then placed on freeze drier overnight. The dried particles were then resuspended in 1 mL of 70% ethanol and stored at 4° C. for future use.

Example 8: Preparing Dendritic Cells Containing Tumor Lysate Loaded Particles

The tumor lysate loaded YCWPs in 70% ethanol suspension was centrifuged. The ethanol was removed carefully and replaced with 1 mL of PBS. The loaded YCWPs were sonicated. The loaded YCWPs were washed with sterile 1×PBS. After final wash, the loaded YCWPs were resuspended in PBS to approximately $1\times10^8$ particles/100 µl PBS.

The loaded YCWPs were added to a dendritic cell culture at a ratio of 1:100, and the culture was returned to 37° C. incubator. Subsequently, the following factors were added to the culture: 50 µg/mL of TNF-α in sterile water was added to the culture at a ratio of 1:5000 in volume (2 µL per 10 mL of culture); 10 µg/mL of 1β in sterile water was added to the culture at a ratio of 1:1000 in volume; 10 µg/mL of IL-6 in sterile water was added to the culture at a ratio of 1:1000 in volume; and 1 µg/mL of PGE2 in 100% ethanol was added to the culture at a ratio of 1:1000 in volume. After all factors were added and mixed into the culture, the culture was incubated overnight.

Example 9: Harvest of Dendritic Cells, Preparation and Cryopresrvation of Vaccine The dendritic cell culture prepared according to Example 9 was removed from the incubator. The following procedure was performed in a hood under sterile conditions. 10 mL of media were removed from culture flask. The culture flask was rinsed with 4.0-4.5 mL of 1×PBS and also added to the media.

1.5-2.0 mL of CellStripper™ was added to the culture flask. The culture flask was placed in 37° C. incubator for 10-20 minutes. About 4 mL of the culture media were added back to the flask from the tube to wash and remove cells. The flask was washed to harvest as many cells as possible. The cells were counted on hemacytometer or Cellometer™. The supernatant was removed after centrifugation.

Subsequently, the cells were resuspended in CryoStor™ 10 at $5\times10^6$ cells/mL, aliquoted into cryovials properly labeled with patient ID Number, date and cell concentration at $1.25\times10^6$ cells/mL per vial (about 250 µL) A 250-500 µL portion was saved in a cryovial for sterility testing, and the remaining vials were stored in Styrofoam containers and placed under −86° C. to step down freeze.

Example 10: Preparation of the Solid Tumor Vaccine for Patient Administration

One cryovial of patient's cell was removed from cryostorage and carefully thawed at 37° C. in a water bath. Under sterile conditions, 1 mL of sterile saline for injection with 5% human serum albumin (or 1 mL of sterile 1×PBS) was gently added to the cryovial containing the cells. After the cells were carefully resuspended, the entire volume from the cryovial was drawn and the syringe containing the tumor cells was used for administration of the vaccine to a patient.

Example 11: Dendritic Cells Containing Tumor Lysate Loaded Particles Versus Antigen Pulsed Dendritic Cells (DCs)

B3Z cells are a T cell hybridoma expressing a T-cell receptor that specifically recognizes the $OVA_{(257-264)}$ (SIINFEKL) epitope in the context of $H-2K^b$ and carry a beta-galactosidase (lacZ) construct driven by a nuclear factor of activated T cells elements from the interleukin 2 promoter (X). These B3Z cells were used to evaluate the effectiveness of dendritic cells pulsed with ovalbumin versus those loaded with ovalbumin by way of ovalbumin loaded YCWPs for antigen presentation, resulting in a CD8+ T cell response.

Figure 6:
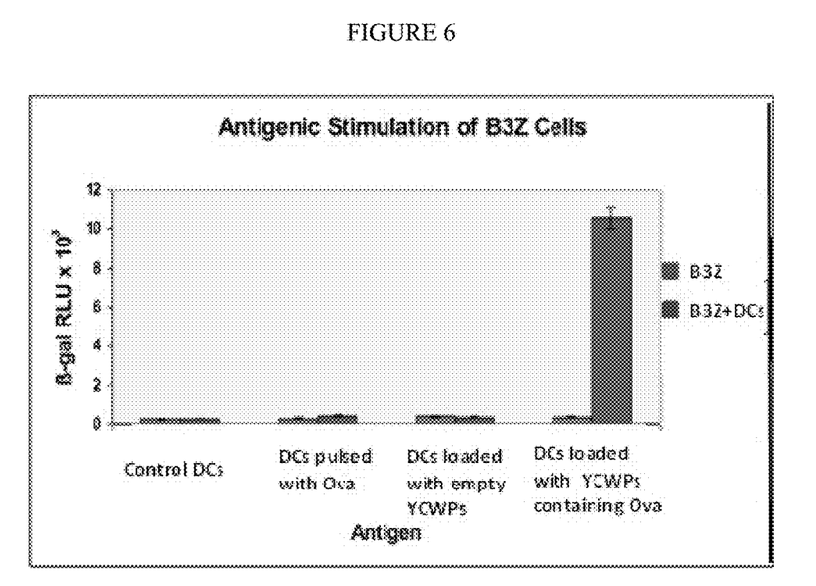
FIG. 6 is a graph comparing the effect of tumor lysate particle loaded dendritic cells versus antigen pulsing of dendritic cells on B3Z cells.

Upon activation by interaction with MHC class I molecules on dendritic cells presenting ovalbumin epitopes, the B3Z cells were engineered to respond by expressing β-galactosidase. β-Galactosidase catalyzes a breakdown of X-gal (5-bromo-4-chloro-indolyl-β-D-galactopyranoside) to yield 5-bromo-4-chloro-3-hydroxyindole, a blue colored product. Spectroscopic measurement of this blue color gives a measure of the effective MHC class I presentation of the ovalbumin epitope. The results of this experiment, shown in FIG. 6, demonstrate that loading dendritic cells by ovalbumin loaded YCWPs gave more than a 100 fold increase in CD8+ T cell response over dendritic cells pulsed with ovalbumin.

Example 12: In Vitro Data

Dendritic cells were prepared from cells obtained from the bone marrow of the femur and tibia of both hind legs of a female C57BL/6J mouse. B16F0 murine melanoma cells were obtained (ATCC (CRL-6322)) and cultured using standard tissue culture techniques. The dendritic cells were loaded with YCWPs containing B16F0 tumor lysate (around $2 \times 10^{-15}$ g/YCWP) at a ratio of 100:1 particles:DC by adding the particles at day 7 of a dendritic cell culture for a period of 2 hours. Three days prior to the preparation of the dendritic cells containing tumor lysate loaded particles, female C57BL/6J mice were challenged with $0.75 \times 10^6$ B16F0 melanoma cells in 0.4 ml 1×PBS by intravenous injection. Once the dendritic cells containing tumor lysate loaded particles were prepared, each mouse in the treatment group was injected intravenously with $2 \times 10^6$ of dendritic cells containing tumor lysate loaded particles and this vaccination was repeated for three weekly doses. The mice were monitored up to four weeks for pulmonary metastasis.

At the end of four weeks (when one of the control mice died), the mice were sacrificed and any occurrence of metastases was counted. All four control animals that were not treated with dendritic cells containing tumor lysate loaded particles had more than 50 tumors. However, none of the treated animals had measurable metastases. This data indicates that dendritic cells containing tumor lysate loaded particles is effective in treating cancer in a proven animal model system. The data are compiled in Table 1.

TABLE 1

Number of Metastases in Control and Treated Mice

| Group | Number of Metastases (including tumors at non-lung sites) |
|---|---|
| Control: | |
| A | >50 |
| B | >50 |
| C | >50 |
| D | >50 |
| Treated: | |
| A | 0 |
| B | 0 |
| C | 0 |
| D | 0 |

Figure 7A:
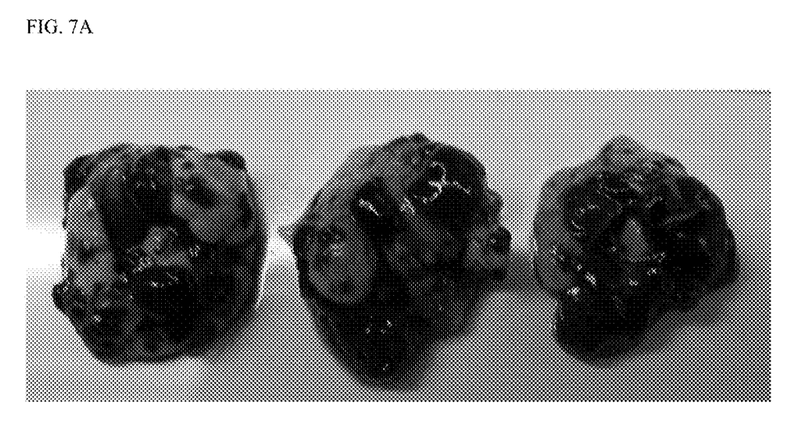
FIG. 7A shows the lungs of control mice afflicted with B16F0 murine melanoma.
Figure 7B:
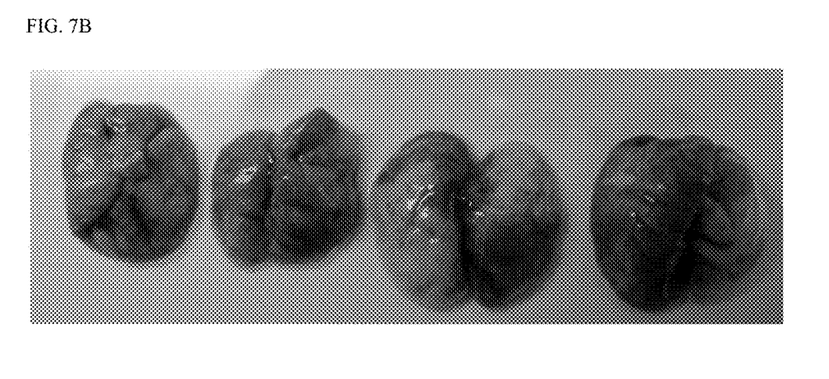
FIG. 7B shows the lungs of mice afflicted with B16F0 murine melanoma but treated with tumor lysate particle loaded dendritic cells.

Moreover, FIG. 7A shows the lungs of three of the control mice (one mouse died prior to the end of the experiment and the lungs were not able to be photographed) in this experiment and FIG. 7B shows the lungs of the four treated mice.

Example 13: In Vivo Procedure

To vaccinate a subject, a dose of 1.25 million dendritic cells containing tumor lysate loaded particles can be cryopreserved in 0.2 mL of a serum-free, 10% dimethyl sulfoxide freezing medium (CryoStor™ CS-10, BioLife Solutions, Inc.). Before injection, the dendritic cells can be thawed and diluted to a 1 mL with sterile saline for injection containing 5% human serum albumin (Albuminar −25, Aventis Behring). The dilution can then be transferred to a 3.0 cc syringe for injection and using a needle no smaller than 23 gauge, which should be administered within 2 hours of the thawing. The injection can be administered subcutaneously into an area of lymph nodes.

Example 14: Isolation of Mononuclear Cells from Whole Peripheral Blood Using the SepMate-50 System Procedure:

| STEP | PROCEDURE/WORK INSTRUCTIONS |
|---|---|
| 1 | Add 15mL of lymphocyte separation medium (LSM) to each SepMate tube by carefully, yet quickly, pipetting it through the central hole of each tube insert. |
| 2 | Pool the whole blood. |
| 3 | Dilute the whole blood sample with twice the initial blood volume of 1xPBS. |
| 4 | Add 30 mL diluted blood to the Sepmate tubes. |
| 5 | Centrifuge for 10-15 minutes at room temperature. |
| 6 | Pour off the top layer containing the enriched PBMC's from each Sepmate tube into new centrifuge tubes. |
| 7 | Cap tubes and centrifuge 5 minutes. |
| 8 | Resuspend pellet in each tube with up to 1.0 mL ACK lysing buffer with pipette. Repeat cycles of adding 1X PBS to resuspend pellet and centrifuge. |
| 9 | Decant the supernatant, and aliquot $50 \times 10^6$ cells suspended in 15 mL RPMI media per flask. Place in the $CO_2$ incubator at 37° C. for 1-1.5 hours. |
| 10 | Remove flasks from incubator. Wash pellet with 1X PBS. |
| 11 | add 15 mL complete DC Media (containing IL-4, GM-CSF, and Gentamycin) and place in the 37° $CO_2$ incubator for 22-24 hours. |
| 12 | On Day 2, continue with inoculation of cultures with YWCP's and cytokines after the dendritic cells have incubated at 37° C. for approx. 22 hours. |

Example 15: Generation of Dendritic Cells Combined with Loaded YCWP's

Following the procedure in Example 14, the following methods are performed:
I. Addition of YCWP's

| STEP | PROCEDURE/WORK INSTRUCTIONS |
|---|---|
| 1 | To each dendritic cell culture flask, add a sufficient volume of tumor lysate infused YCWP's at a ratio of 1:100. (50-200 ul) and incubate for 1-2 hours. |

II. Preparation and Addition of Cytokines

| STEP | PROCEDURE/WORK INSTRUCTIONS |
|---|---|
| 1 | Add TNF-α, 1β, IL-6 and PGE2 to each culture flask, |

Example 16: Harvest of Cells, Preparation and Cryopreservation of Vaccine

Following the procedure in Example 15, the following methods are performed:

Harvest of Cells:

| STEP | PROCEDURE/WORK INSTRUCTIONS |
|------|------------------------------|
| 1 | Add 4.0-4.5 mL 1xPBS to each flask containing 10 mL media. |
| 2 | Add 1.5-2.0 mL CellStripper ™ to each flask to release mature cells and incubate at 37 C. |
| 3 | Centrifuge and emove supernatant by decanting until 'dry' pellet remains. |

II. Preparation of Vaccine and Cryopreservation:

| STEP | PROCEDURE/WORK INSTRUCTIONS |
|------|------------------------------|
| 1 | Resuspend cells in CryoStor ™ 10, aliquot and step down freeze. |

What is claimed is:

1. A composition comprising a yeast cell wall particle and a tumor lysate, wherein about 200 µg to about 500 µg tumor lysate is loaded within about $10^9$ yeast cell wall particles.

2. The composition of claim 1, wherein the yeast cell wall particle is about 0.5 µm to about 5 µm in size.

3. The composition of claim 1, wherein the tumor lysate is present in an amount of about 200 µg.

4. The composition of claim 1, wherein the tumor lysate is a lysate of a cancer selected from the group consisting of breast cancer, small cell lung cancer, non-small cell lung cancer, glioma, medulloblastoma, neuroblastoma, Wilms tumors, rhabdomyosarcoma, osteosarcoma, liver cancer, pancreatic cancer, melanoma, prostate cancer and ocular melanoma.

5. The composition of claim 1, further comprising a dendritic cell, wherein the tumor lysate loaded particle is phagocytosed by the dendritic cell.

6. The composition of claim 5, wherein the dendritic cell is an immature cell that has been isolated for no more than 8 days.

7. A method for producing a vaccine comprising the composition of claim 1 comprising:
 (i) contacting a yeast cell wall particle with a tumor lysate; and
 (ii) freeze drying the tumor lysate and the yeast cell wall particle to produce the tumor lysate loaded yeast cell wall particle,
 wherein about 200 µg to about 500 µg tumor lysate is loaded within about $10^9$ yeast cell wall particles.

8. The method of claim 7 further comprising
 (iii) resuspending the freeze-dried yeast cell wall particle of (ii); and
 (iv) freeze-drying the resuspended solution.

9. The method of claim 7, further comprising incubating the tumor lysate loaded particle with a dendritic cell such that the cell phagocytoses the particle.

10. The method of claim 9 further comprising cryopreserving the dendritic cell comprising the phagocytosed loaded particle.

11. The method of claim 7, wherein step (i) further comprises: (a) adding tumor lysate to the yeast cell wall particle, (b) incubating the yeast cell wall particle, (c) freeze-drying the yeast cell wall particle and (d) washing the yeast cell wall particle, wherein steps (b)-(c) are repeated at least once with a step of adding water into the yeast cell particle before step (b) is repeated.

12. The method of claim 9, wherein the tumor lysate loaded particle and the dendritic cell are incubated in a ratio of about 100:1 for 1 to 2 hours, followed by collecting and washing of the dendritic cell.

13. A method for treating cancer comprising administering the composition of claim 1 to a patient in need thereof.

14. The method of claim 13, wherein the cancer is selected from the group consisting of breast cancer, small cell lung cancer, non-small cell lung cancer, glioma, medulloblastoma, neuroblastoma, Wilms tumor, rhabdomyosarcoma, osteosarcoma, liver cancer, pancreatic cancer, melanoma, prostate cancer and ocular melanoma.

* * * * *